(12) United States Patent
Tamayo

(10) Patent No.: US 10,137,035 B1
(45) Date of Patent: *Nov. 27, 2018

(54) ROUND POSTERIOR CAPSULOTOMY FOR THE OPACIFICATION OF A POSTERIOR CAPSULE AND LENS

(76) Inventor: Gustavo Tamayo, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/602,142

(22) Filed: Sep. 1, 2012

Related U.S. Application Data

(60) Provisional application No. 61/635,894, filed on Apr. 20, 2012.

(51) Int. Cl.
*A61F 9/008* (2006.01)

(52) U.S. Cl.
CPC ...... *A61F 9/008* (2013.01); *A61F 2009/0087* (2013.01); *A61F 2009/00887* (2013.01)

(58) Field of Classification Search
CPC ... A61B 18/18; A61B 3/10; A61F 2/16; A61F 2/10; A61F 9/007; A61K 9/00; A61M 31/00; A61L 15/00; G01B 11/02
USPC ............... 606/4, 6; 623/6.15; 424/429, 445; 356/508; 351/221; 604/521
See application file for complete search history.

(56) References Cited

U.S. PATENT DOCUMENTS

| | | | | |
|---|---|---|---|---|
| 4,412,359 A * | 11/1983 | Myers | | 623/6.15 |
| 5,366,501 A * | 11/1994 | Langerman | | A61F 2/1694 623/6.42 |
| 6,027,531 A * | 2/2000 | Tassignon | | A61F 2/16 623/6.4 |
| 6,099,522 A * | 8/2000 | Knopp | | B23K 26/04 606/10 |
| 6,986,763 B2 * | 1/2006 | Holmen | | 604/521 |
| 7,330,275 B2 * | 2/2008 | Raksi | | 356/508 |
| 7,597,444 B2 * | 10/2009 | Rathjen et al. | | 351/221 |
| 8,414,564 B2 * | 4/2013 | Goldshleger et al. | | 606/4 |
| 2003/0208265 A1 * | 11/2003 | Ho | | A61F 2/1616 623/4.1 |
| 2004/0047900 A1 * | 3/2004 | Allan | | 424/445 |
| 2006/0195076 A1 * | 8/2006 | Blumenkranz et al. | | 606/4 |
| 2008/0161781 A1 * | 7/2008 | McArdle et al. | | 606/6 |
| 2008/0193504 A1 * | 8/2008 | Menko | | 424/429 |
| 2009/0012507 A1 * | 1/2009 | Culbertson et al. | | 606/6 |
| 2009/0069794 A1 * | 3/2009 | Kurtz | | 606/4 |
| 2009/0171327 A1 * | 7/2009 | Kurtz et al. | | 606/6 |
| 2010/0042079 A1 * | 2/2010 | Frey et al. | | 606/4 |
| 2011/0178511 A1 * | 7/2011 | Blumenkranz et al. | | 606/4 |
| 2011/0178512 A1 * | 7/2011 | Blumenkranz et al. | | 606/6 |
| 2011/0196350 A1 * | 8/2011 | Friedman et al. | | 606/6 |

(Continued)

OTHER PUBLICATIONS

Roger F. Steinert, MD, Nd:YAG Laser Posteror Capsulotomy, on-line http://one.aao.org/, Nov. 4, 2013.*

(Continued)

*Primary Examiner* — Gary Jackson
*Assistant Examiner* — Zahed Kabir
(74) *Attorney, Agent, or Firm* — Arrubla | Taylor PA; Andres F. Arrubla, Esq.

(57) ABSTRACT

The present invention is in the field of ophthalmology and relates to methods of performing a generally round posterior capsulotomy, preferably in a continuous manner, without disturbing an intraocular lens, and without inducing any pressure changes inside the eye. The posterior capsulotomy comprises performing a generally round circular posterior capsulotomy using a suitable ophthalmic laser device.

9 Claims, 5 Drawing Sheets

(56) References Cited

U.S. PATENT DOCUMENTS

2011/0270389 A1* 11/2011 Glazer ................. A61F 2/1635
623/6.37
2012/0089134 A1* 4/2012 Horvath et al. ................. 606/6

OTHER PUBLICATIONS

Aron-Rosa et al., Use of a pulsed neodymium Yag laser (picosecond) Ophthalmic Surg. Jul. 1981;12(7):496-9. PubMed—indexed for MEDLINE.*
Tariq M. Aslam, MRCSEd, Use of Nd:YAG Laser Capsulotomy, Survey of Ophthalmology vol. 48 • No. 6 • Nov.-Dec. 2003, 2003 by Elsevier Inc.*
Daniele Aron-Rosa, M.D. et al. Use of the neodymium-yag laser to open. AM Intra-Ocular Implant Soc J-vol. 6, Oct. 1980.*
Tariq Mehmood Aslam, Baljean Dhillon Neodymium:YAG laser capsulotomy: a clinical morphological analysis. Graefe's Arch Clin Exp Ophthalmol (2002) 240:972-976.*

* cited by examiner

ROUND POSTERIOR CAPSULOTOMY FOR THE OPACIFICATION OF A POSTERIOR CAPSULE AND LENS

RELATED APPLICATIONS

This application claims priority to U.S. Provisional Patent Application No. 61/635,894, filed on Apr. 20, 2012, the contents of which are relied upon and incorporated by reference.

FIELD OF THE INVENTION

The present invention relates to a method of treating certain cataract post-treatment secondary symptoms and, more specifically, a method of treating the opacification of the posterior lens and/or capsule. In contrast to current Posterior Capsulotomy techniques, the Posterior Capsulotomy technique of the present invention can be performed to reduce irregular borders and/or eliminate sharp converging cuts to thereby considerably reduce marry associated risks.

BACKGROUND OF THE INVENTION

Cataract surgery treatments are among, if not, the most common ophthalmic procedures in the entire world. Cataract surgery post treatment symptoms and complications are often due to the opacification of the posterior lens and capsule. Opacification is a common reoccurring complication of many current cataract surgery procedures. As a result, new methods of treatment that minimize or reduce risks associated are particularly desirable.

New improved posterior capsulotomy cutting tools such as, knives, heating tools to remove the tissue and laser apparatus, types of intraocular lenses, and active agent solutions continue to be developed and described in recent references to address the need of improved ocular procedures. For example:

U.S. Pat. No. 4,955,894 titled "Posterior Capsulotomy Knife," describes a knife that seeks to minimize or eliminate vitreous loss during the capsulotomy procedure by inflicting a minimal wound.

U.S. Pat. No. 4,648,879 titled "Posterior Chamber Intraocular Lens," describes an Intraocular Lens that may be placed in the posterior capsule. The new Lens which may be safely perforated with a laser beam transversely to a line of tension formed by the projection, causing the posterior capsule to tear and form an opening to eliminate any cloudiness of the posterior capsule from behind the optic. The perforation being safe in part due to the Lens having a pair of rearward projections, each located radially outwardly of opposite peripheral portions of the optica and cooperating to produce a similar tension and spacing effect.

U.S. Pat. No. 7,985,405 titled "Treatment and Method for Preventing Posterior Capsular Opacification by Selectively Inducing Detachment and/or Death of Lens Epithelial Cells," describes a treatment solution used to prevent posterior capsular opacification that can applied or introduced into the lens capsular bag before, during, or after cataract surgery.

Pertaining to the implementation of the present invention, United States Patent Application No. 2011/0118609 titled "Imaging Surgical Target Tissue by Nonlinear Scanning" describes an example of a system for laser surgery based on imaging a target tissue by nonlinear scanning that may be used to implement some parts of the present invention as described in the description section of the present application.

Moreover, opacification of the posterior lens and capsule, (also called Secondary Cataract for the symptoms it produces), is a complication that can generally occur after the insertion of an intraocular lens in patients undergoing cataract surgery with an incidence varying from 10% to 50% of patients. It is manifested by one or more symptoms of; gradual decrease in vision, blurred vision, decrease of visual acuity, ghost imaging, and glare.

Bearing in mind the debilitating symptoms and the fact that all currently established cataract ophthalmic treatments/procedures can include subsequent susceptibility to opacification of the posterior capsule and lens, the treatment of opacification using a method where associated risks are significant reduced becomes a goal of utmost importance for both physicians and patients alike. Presented in the following sections, new methods of treating opacification capable of significantly reducing particular risks and symptoms are the subject matter of the present invention.

SUMMARY DESCRIPTION OF THE INVENTION

Accordingly, the present invention includes a method of treating the opacification of the posterior lens and/or capsule, comprising performing a Generally Round Posterior Capsulotomy procedure performed without entering the eye at one or more critical stages during or after cataract treatments. More specifically, where the Generally Round Posterior Capsulotomy procedure can be performed working directly in the posterior capsule, without disturbing a previously inserted ophthalmic device, such as an intraocular lens, and without inducing any pressure changes inside the eye since the eye can remain closed.

In one aspect of the present invention, a Generally Round Posterior Capsulotomy can be performed to reduce irregular borders and/or eliminate sharp converging cuts to thereby considerably reduce many risks, including for example, the complete rupture of the posterior capsule with the associated vitreous loss. Other risks may also include migration of the new lens to a place other than the capsular bag, retinal detachment, macular edema, corneal edema, and/or an increase in intraocular pressure.

The continuous Generally Round Posterior Capsulotomy of the present invention can be performed using, any type of laser, for example a solid state laser, such as, a yttrium aluminum garnet ("YAG") laser or gas laser. More specifically, in a preferred embodiment, the laser used to perform the Generally Round Posterior Capsulotomy can so through the cornea, anterior chamber and intraocular lens directly into the posterior capsule and/or lens, where it can be focused and administered. The focusing and administration may be done using, for example, a system such as one described in United States Patent Application No. 2011/0118609, one or more suitable slit lamps, microscopes or a combination thereof, many which are already available and regularly used by eye care practitioners during eye surgery.

In another aspect of the present invention, the Generally Round Posterior Capsulotomy procedure of the present invention can correct the opaqueness of the posterior capsule of the capsular bag/lens, which can be caused by cell or fibrotic tissue buildup, wrinkles, folds or even the accumulation of fluid in the space between the lens and the capsule without the resulting in additional retinal stress or sharp converging cuts made during the posterior capsulotomy.

In another aspect of the present invention, carrying out the Generally Round Posterior Capsulotomy can be important in allowing the Physician to solve the problems caused by the compromised posterior capsule, but at the same time, it can help preserve the ability to exchange the intraocular lens in case changing the type of intraocular lens becomes a need and the only possible solution for the preservation of the vision and the abolition of unwanted symptoms for the patient. More specifically, the method may be used to ensure that a capsulotomy is not contradicted when there may be an ultimate need to replace the intraocular lens due to risks associated with current techniques.

In yet another aspect of the present invention, the Generally Round Posterior Capsulotomy can help prevent the increase in diameter over time and avoid complications of large capsulotomy such as retinal holes or detachment as well as, macular edema. Further, the Generally Round Posterior Capsulotomy can help achieve a more accurate target size, as it may be needed. For example, it may be desired that the size is slightly larger to cover the central area of the multifocal lens. The size control can result in a more stable environment, without any influence of the intraocular pressure over its size.

BRIEF DESCRIPTION OF THE DRAWINGS:

The accompanying drawings are incorporated in and constitute a part of this specification. The drawings illustrate several method steps and embodiments of the invention and together with the description serve to explain the invention and shall not be used to limit the inventive principles of the invention.

DETAILED DESCRIPTION

Figure 1:
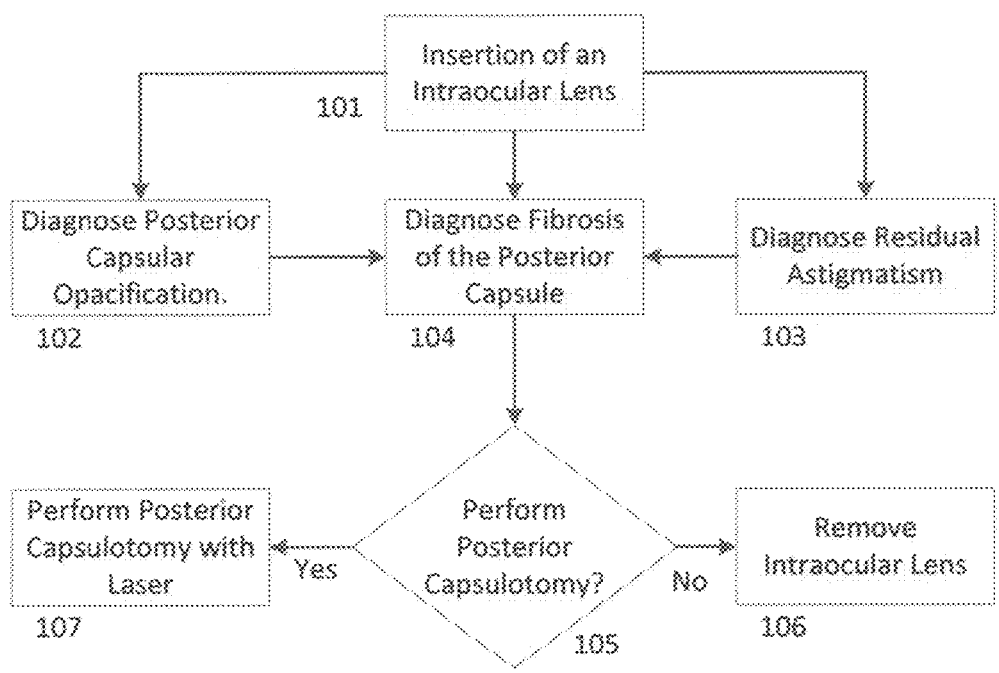
FIG. 1 illustrates a flowchart with method steps that may be implemented to carry out the method of some parts of the present invention.

The present invention relates to methods of treating the opacification of the posterior lens and/or capsule after some ocular treatments. In contrast to current posterior capsulotomy techniques, the methods can be performed to reduce irregular borders and/or eliminate sharp converging cuts and thereby considerably reduce many risks associated with current procedures.

In the following sections, detailed descriptions of embodiments and methods of the invention will be given. The description of both preferred and alternative embodiments though through are exemplary only, and it is understood that to those skilled in the art that variations, modifications and alterations may be apparent. It is therefore to be understood that the exemplary embodiments do not limit the broadness of the aspects of the underlying invention as defined by the claims.

GLOSSARY

"Eye Characteristics" as used herein measurements derived from one or more ophthalmic measuring tests or techniques. For example, eye characteristics can include corneal curvature and corneal topography, ocular motility, and intraocular pressure measurements.

"Generally Round Posterior Capsulotomy" as used herein refers to a posterior capsulotomy ophthalmic procedure that is performed by removing the opaqueness of the posterior capsule and/or lens by performing a capsulotomy in a round, circular, oval, or curvilinear line manner to improve the quality and quantity of visual acuity after the insertion of an intraocular lens. More specifically, the generally round, circular, oval, or continuous curvilinear line manners which can preferably be performed in a continuous manner using a solid state laser, such as, a YAG laser or gas laser. The Generally Round Posterior Capsulotomy can eliminate or significantly reduce irregular borders and sharp converging cuts that increase the risk of many associated complications. Moreover, the Generally Round Posterior Capsulotomy procedure may be performed, for example, whenever the posterior capsule of the capsular bag becomes opaque either by cells or fibrotic tissue or wrinkles and folds or even due to fluid in the space between the lens and the capsule.

The present invention provides as method that may be used as part of or subsequent to many ocular procedures or treatments. Many advantages will be apparent to one skilled in the art from the implementation and use of different methods of the present invention.

Generally Round Posterior Capsulotomy

Manual circular continuous posterior capsulotomy procedures have been described in videos and presentations since the advent of the circular anterior capsulorhexis. However, these existing techniques have to be done in surgery, with instruments inserted inside the eye and in cases where there already is an intraocular lens present, the possibility of success of most current techniques is very limited.

The method of the present invention includes a Generally Round Posterior Capsulotomy procedure that may not require entering the eye and/or disruption of a placed intraocular lens. The Generally Round Posterior Capsulotomy method can be extremely advantageous due to the shape and means of achieving the shape without entering the eye to perform a posterior capsulotomy thereby significantly reducing irregular cuts that can be affected by pressure changes. More specifically, the irregular cuts can go to the equator and to the periphery due to pressure changes, for example, caused by the later exchange of an intraocular lens, often consequently leading to vitreous loss and damage of the capsular bag greatly diminishing the possibility of accurate placement and positioning of a new lens within the posterior capsule.

Furthermore, the Posterior Capsulotomy can be performed working directly in the posterior capsule, without disturbing an inserted ophthalmic device, such as an intraocular lens, and without inducing any significant pressure changes inside the eye. Pressure changes can be minimized or eliminated altogether using systems that allow the eye to be completely closed. The systems for performing a Generally Round Posterior Capsulotomy can preferably be performed using, any type of laser, for example a solid state such as a yttrium aluminum garnet ("YAG") laser or gas laser.

A laser system typically contains a device to create light in a sophisticated and precise manner. The laser uses an electric current a special gas to initiate a reaction that produces some type of light energy. The kind of light, its intensity and the frequencies released from the tube can be precisely controlled for ophthalmology use.

Laser light can reach its maximum strength at the focal point, the point where all the rays of light converge, Once the light passes the focal point, the strength of the beam is rapidly diminished. The YAG laser can produce infrared light impulses which create controlled openings in the targeted tissue through photodisruption. These short bursts of energy that can be used for the Generally Round Posterior Capsulotomy of the present invention.

The shape as defined, is important as well as the manner in which the shape is achieved may be depending on the laser system used. For example, as previously referenced one system described in United States Patent Application No. 2011/0118609 titled "Imaging Surgical Target Tissue by Nonlinear Scanning" describes an example of a system for laser surgery based on imaging a target tissue by nonlinear scanning that may be used to implement some parts of the present invention. A laser system, such as the one described, may be improved to provide more successful cataract treatments and minimize risks when the teachings of the present invention are implemented.

Carrying out a contiguous Generally Round Posterior Capsulotomy in the described manner can result in various advantages. For example, the presence of a continuous Generally Round Posterior Capsulotomy of the desired or needed diameter, will be extremely important in allowing the Physician to solve the problems caused by the compromised posterior capsule, but at the same time, it can help preserve the ability to exchange the intraocular jobs in case changing the type of intraocular lens becomes a need and the only possible solution for the preservation of vision.

The continuous Generally Round Posterior Capsulotomy can eliminate or significantly reduces sharp converging edges which are the causes of various complications further described in other parts of this invention when the lens has to be replaced. The preferred manner includes the lasers focus point to be directed in a continuous manner in a Generally Round manner and starting at a point that serves as both the starting and ending point to thereby eliminating any additional connecting points. This is important as the tissue that is being disrupted can move and the more points where for connection increases the probability of forming unintended sharp conversing edges.

Some laser systems that may be implemented can preferable include a smart laser system that identifies the desired one or more points used as starting and ending points in three dimensional space in relation to the characteristics of neighboring tissue. For example, an imaging system that functions prior to and during the capsulotomy to identify characteristics of neighboring tissue, such that, if during the continuous Generally Round Capsulotomy disrupted tissue or parts move significantly to warrant the originally calculated path and shape of the capsulotomy to change, the movement can be accounted for to avoid the undesired disruption of neighboring tissue. Additionally, if the point in three-dimensional space moves, the accuracy for starting and ending at the same point in three dimensional space can be improved using the smart laser system. The imaging system may include for example an optical coherence tomography (OCT) imaging system.

In another aspect of the present invention, the continuous Generally Round Posterior Capsulotomy can prevent the increase in diameter over time and avoid complications of large capsulotomy such as retinal holes or detachment, as well as, macular edema. Also, the posterior capsulotomy can better achieve a more accurate target size, as needed. For example, it may be desired that the size is slightly larger to cover the central area of the multifocal lens. The size control can result in a more stable environment without any influence of the intraocular pressure over its size.

Referring now to FIG. 1, a flowchart with method steps that may be implemented to perform a continuous Generally Round Posterior Capsulotomy without the need of entering the eye is depicted. At 101, the insertion of an intraocular lens occurs as part of a cataract treatment. After the insertion has taken place, and one or more of; diagnosis of posterior capsular opacification 102, diagnosis of fibrosis of the posterior capsule 104, and diagnosis of residual astigmatism 103 takes place, a Posterior Capsulotomy may be warranted 105. By performing the continuous Generally Round Posterior Capsulotomy, the risks described due to converging edges and sharp edges can be minimized so that if it is subsequently determined that there is a need to remove the lens 106, the ophthalmologist can perform replace the Intraocular Lens after the posterior continuous Generally Round Posterior Capsulotomy is performed without contradiction.

Figure 2:
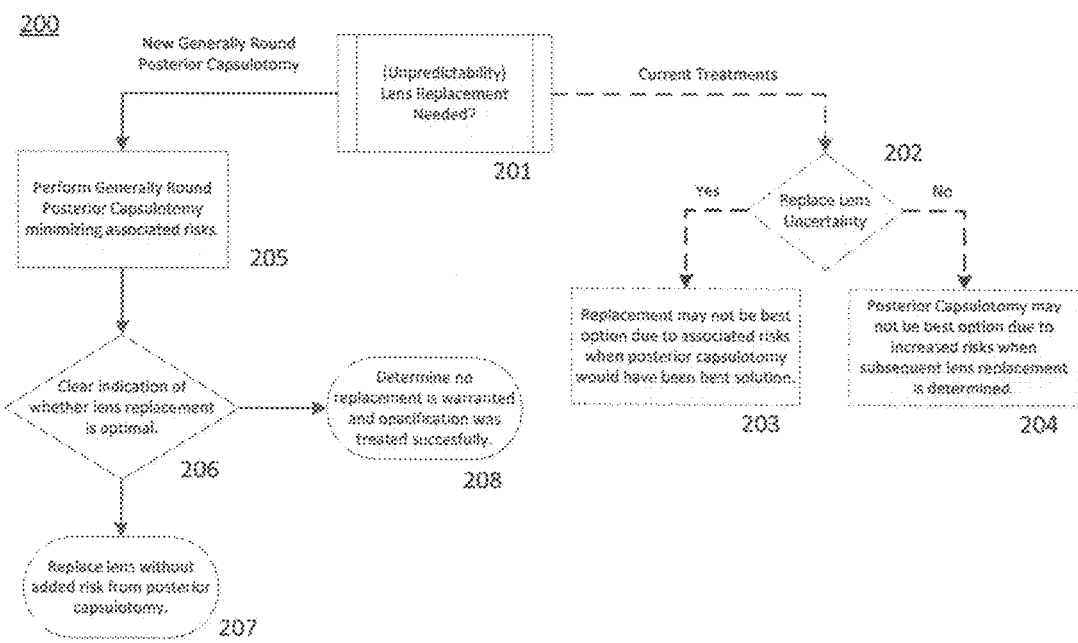
FIG. 2 illustrates a flowchart with method steps to ensure risks factors are eliminated in some pans of cataract treatments in accordance to some aspects of the present invention.

Referring now to FIG. 2, a flowchart with method steps to help explain the importance of 106 at FIG. 1 are depicted. More specifically, why ensuring derivatives of the existing posterior capsulotomy treatments associated with resulting risks, during subsequent intraocular lens replacement are significantly minimized or reduced as part of a cataract treatment 200. At 201 a physician encounters a level of unpredictability regarding on whether the replacement of a lens is required. Using current treatments, the uncertainty 202 can result in either the physician replacing the lens without knowing this would have been required 203, or alternatively, the physician can perform a posterior capsulotomy and increase the risk of subsequent lens replacement if it is needed 204.

To the contrary, by performing the continuous Generally Round Posterior Capsulotomy, the posterior capsulotomy may be performed every time since the subsequent associated risks during the lens replacement can be eliminated or minimized 205. This can result in the physician having a clear indication of whether lens replacement is the optimal solution 206. Lens replacement may not be necessary 208 and therefore the opacification can be successfully treated with the continuous Generally Round Posterior Capsulotomy 208, or the lens may be replaced at a later time without the added risk from the capsulotomy 207. Either way, the patient can benefit from avoiding unnecessary lens replacement and the increased risks from the capsulotomy.

Figure 3:
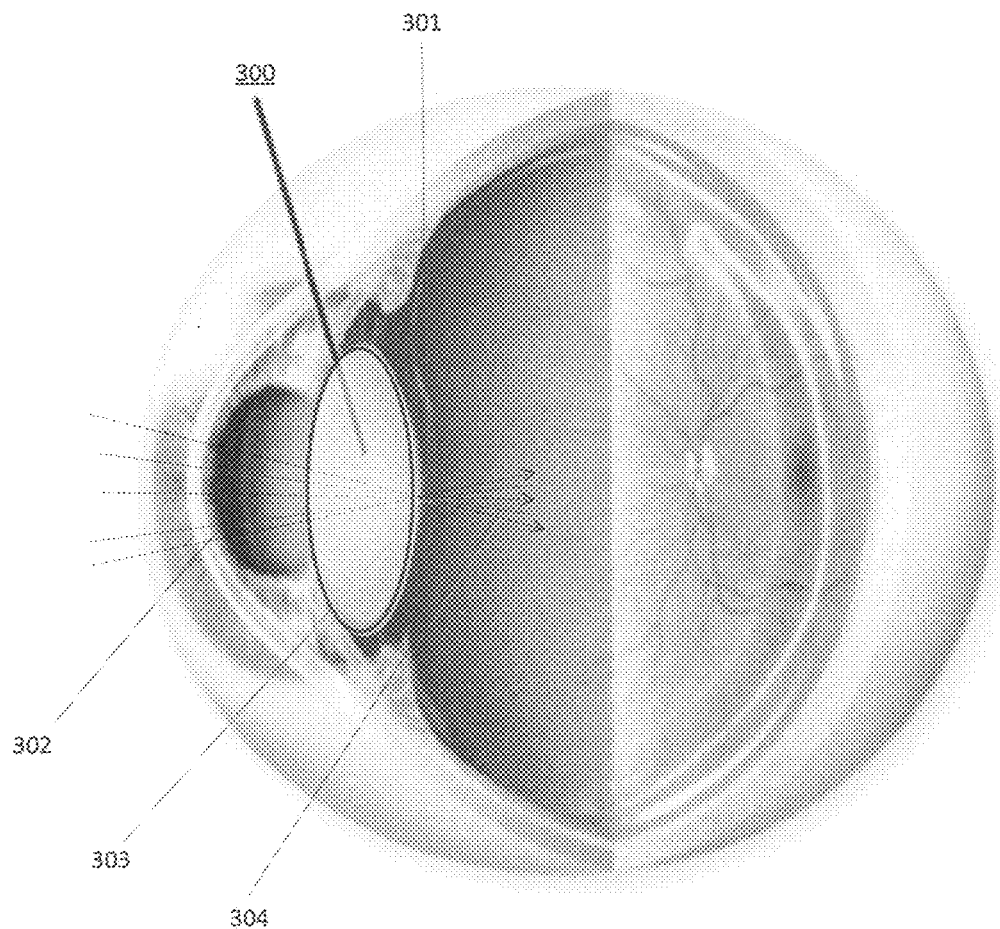
FIG. 3 illustrates a cross section of an eye with an exemplary laser representation that may be used for a Generally Round Posterior Capsulotomy.

Referring now to FIG. 3 a cross section of an eye with a laser representation for a circular posterior capsulotomy is depleted. At 302 rays of a laser beam are shown passing through the cornea and ophthalmic lens implant 300. More importantly, in a preferred embodiment, the laser used to perform the continuous Generally Round Posterior Capsulotomy can go through the cornea, anterior chamber and intraocular lens directly into the posterior capsule and can be administered and focused accordingly. The administration and focusing may be done using, for example, one or more suitable slit lamps, microscopes or a combination thereof, many which are already available for use in eye surgery.

As the beam reaches its focal point 303 on the cloudy capsule 302, the energy becomes highly concentrated causing disruption of the tissue thereby creating a small generally round or round opening that can then moved in a continuous curvilinear manner. After the focal point, the vectors of light can continue in different directions 304 accordingly to avoid any significant unwanted disruption of the tissue.

Figure 4:
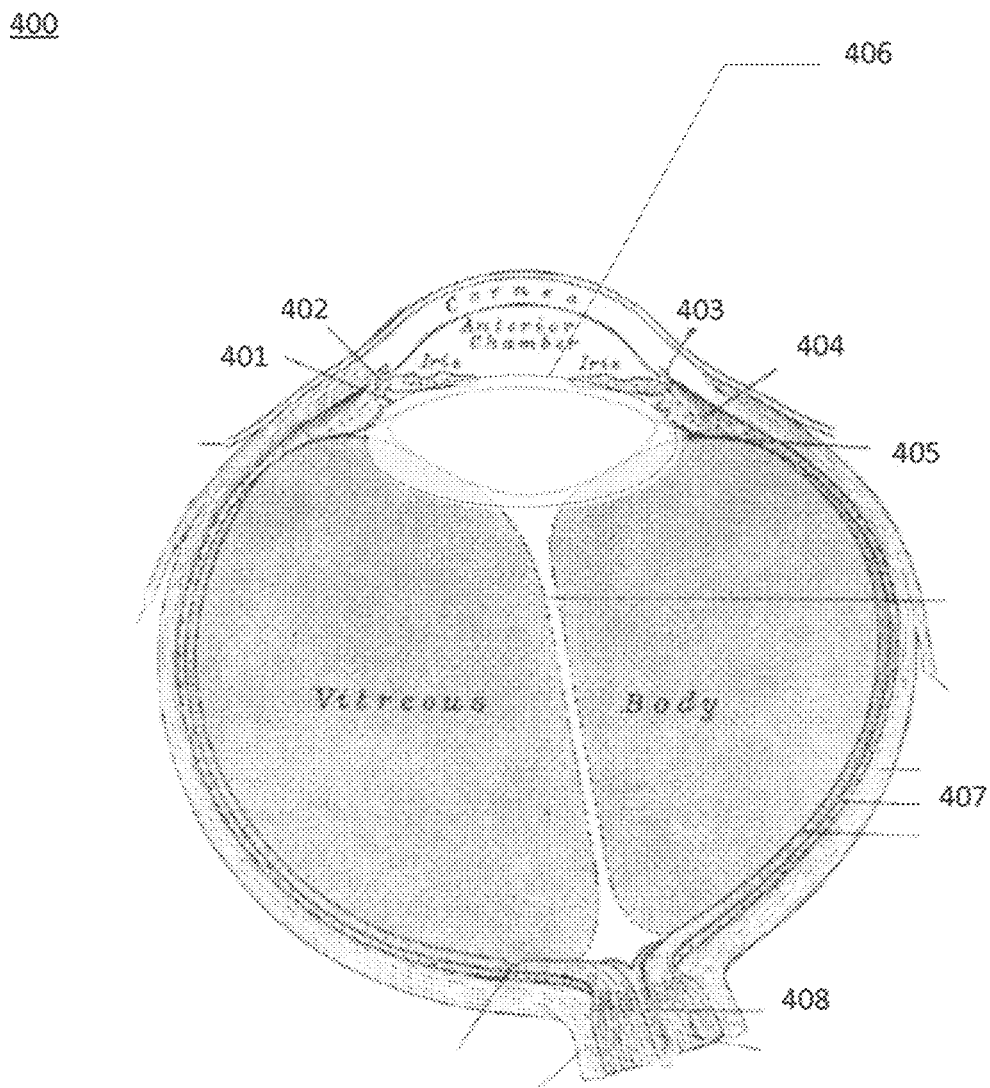
FIG. 4 illustrates another representation of an eye and respective pans associated with in some aspects of the method of performing the Generally Round Posterior Capsulotomy of the present invention.

Referring now to FIG. 4, another representation of an eye and respective parts associated with in some aspects of the method of performing the Generally Round Posterior Capsulotomy of the present invention is depleted. The lens 405, surrounded by the iris 401-404 is located behind the anterior chamber and the cornea. At 406, a region in which the opacification can occur is depicted. The vitreous is also depicted being in contact with the retina 407 but it is not adhered to the retina 407, except at the optic nerve disc 408. Therefore, unlike the fluid in the frontal parts of the eye (aqueous humour) which is continuously replenished, the gel in the vitreous chamber is stagnant and if cells or other byproducts get into the vitreous, they will remain there unless removed surgically. As a result, it is vital that the pressure changes from the vitreous body are controlled and minimized to avoid changing the position of the lens in the posterior chamber causing the many disastrous consequences previously described.

Figure 5A:
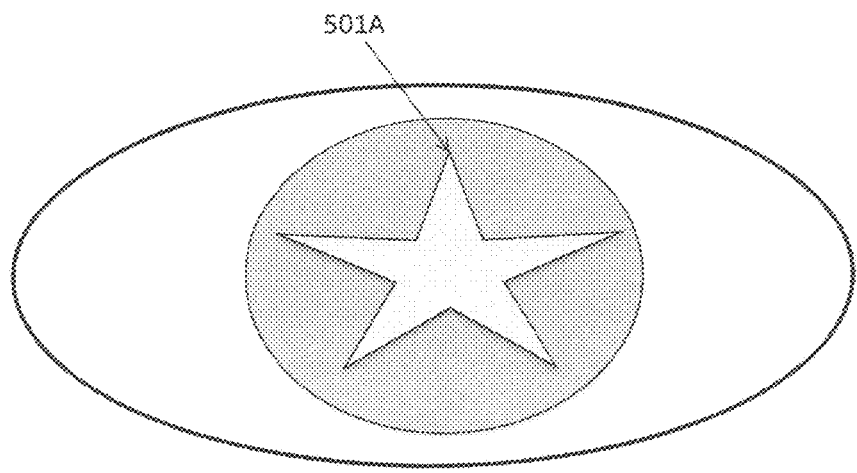
FIG. 5A illustrates an exemplary ophthalmic capsulotomy procedure as performed today.
Figure 5B:
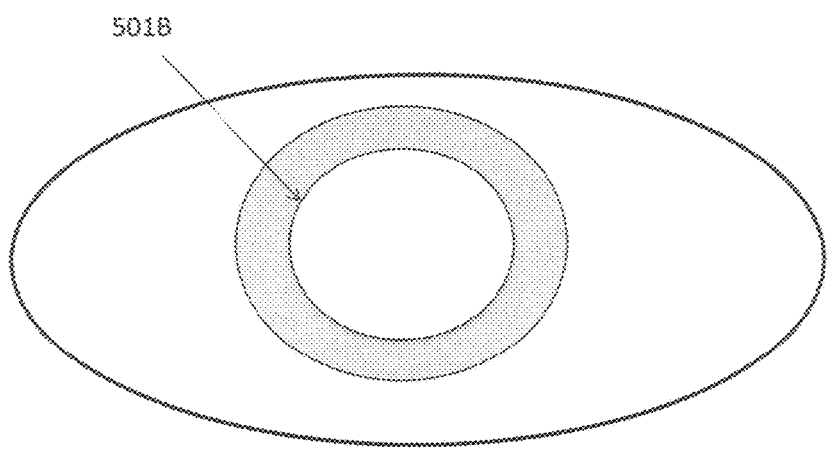
FIG. 5B illustrates an exemplary ophthalmic capsulotomy procedure in a manner consistent with the Generally Round Posterior Capsulotomy method of the present invention.

FIG. 5A illustrates an exemplary ophthalmic capsulotomy procedure as performed today. At 500A, a capsulorhexis procedure as performed and known today is depicted. The procedure which can include sharp borders 501 which may continue toward the periphery with pressure changes. FIG. 5B illustrates an exemplary ophthalmic capsulotomy procedure in a manner consistent with the Generally Round Posterior Capsulotomy method of the present invention. The exemplary capsulorhexis 500B is performed in a curvilinear continuous manner 501B resulting in significantly higher tolerance to pressure changes. The ability to tolerate the higher pressure changes then can eliminate risks and allow for the ophthalmologist to perform the procedure at different stages during treatments thereby eliminating uncertainty, unwarranted intraocular lens replacement resulting risks, etc.

CONCLUSION

A number of embodiments of the present invention have been described. While this specification contains many specific implementation details, there should not be construed as limitations on the scope of any inventions or of what may be claimed, but rather as descriptions of features specific to particular embodiments of the present invention.

Certain features that are described in this specification in the context of separate embodiments can also be implemented in combination in a single embodiment. Conversely, various features that are described in the context of a single embodiment can also be implemented in combination in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while method steps are depicted in the drawings in a particular order, this should not be understood as requiring that such steps be performed in the particular order shown or in sequential order, or that all illustrated operations be performed, to achieve desirable results. In certain circumstances, multitasking and parallel may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order show, or sequential order, to achieve desirable results. In certain implementations, multitasking and parallel processing may be advantageous. Nevertheless, it will be understood that various modifications may be made without departing from the spirit and scope of the claimed invention.

What is claimed is:

1. A method of treating loss of visual quality and acuity from changes of a posterior capsule of an eye the method comprising:
   examining characteristics of a patient's eye after surgery for insertion of an intraocular lens;
   determining that one or more of: opaque cells, fibrotic tissue, wrinkles in a posterior capsule, folds in the posterior capsule and fluid in a space between the inserted intraocular lens and the posterior capsule, has occurred:
   determining a start point and an end point in three dimensional space on the posterior capsule of the patient's eye; and
   performing a Generally Round Posterior Capsulotomy in a continuous manner, eliminating irregular borders and sharp converging cuts, while the intraocular lens remains inserted in the eye, wherein the Generally Round Posterior Capsulotomy is based upon the determined start point and end point and comprises a generally round shape that prevents an increase in diameter over time and prevents loss of vitreous in the patient's eye and the performing of the Generally Round Posterior Capsulotomy does not induce pressure changes inside the eye.

2. The method of claim 1, wherein said Generally Round Posterior Capsulotomy is performed with an ophthalmic laser system and a location of the start point and the end point in three dimensional space and a size of Generally Round Posterior Capsulotomy is based at least in part upon a size and shape of the intraocular lens inserted in the patient's eye.

3. The Method of claim 2, wherein the laser comprises an ophthalmic neodymium-YAG laser system.

4. The Method of claim 3, wherein the laser system is capable of projecting through a cornea in the eye without resulting in any significant changes until the posterior capsule is reached.

5. The Method of claim 2, wherein the ophthalmic laser system additionally comprises an OCT imaging system.

6. The Method of claim 1, additionally comprising the step of imaging targeted tissue and surrounding tissue during the Generally Round Posterior Capsulotomy.

7. The Method of claim 1, wherein the starting point is in three dimensional space for the continuous Generally Round Posterior Capsulotomy is a same ending point for each laser projection.

8. The Method of claim 7, wherein the starting point in the starting point in three dimensional space is monitored in relation with the surrounding tissue to account for any changes that may occur during Generally Round Posterior Capsulotomy.

9. The Method of claim 1, additionally comprising the step of replacing the intraocular lens subsequent to the Generally Round Posterior Capsulotomy.

* * * * *